United States Patent
Duan

(10) Patent No.: US 6,479,619 B1
(45) Date of Patent: Nov. 12, 2002

(54) SULFOISOPHTHALIC ACID SOLUTION PROCESS THEREWITH

(75) Inventor: Jiwen F. Duan, Apex, NC (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 6 days.

(21) Appl. No.: 09/808,663

(22) Filed: Mar. 15, 2001

(51) Int. Cl.$^7$ ............................................. C08G 63/78
(52) U.S. Cl. ........................ 528/286; 528/271; 528/272
(58) Field of Search ................................ 528/286, 271, 528/272

(56) References Cited

U.S. PATENT DOCUMENTS

| | | |
|---|---|---|
| 4,611,049 A | 9/1986 | Kuratusuji et al. |
| 5,097,004 A | 3/1992 | Gallagher et al. |
| 5,559,205 A | 9/1996 | Hansen et al. |
| 6,075,115 A | 6/2000 | Putzig et al. |

FOREIGN PATENT DOCUMENTS

| | | |
|---|---|---|
| EP | 0 847 960 A1 | 6/1998 |
| EP | 1 006 220 A1 | 6/2000 |
| JP | 7-209811 | 8/1995 |
| JP | 9-40855 | 2/1997 |
| JP | 9-59601 | 3/1997 |
| JP | 9-249742 | 9/1997 |
| JP | 10-287740 | 10/1998 |
| JP | 11-29630 | 2/1999 |
| JP | 11-29685 | 2/1999 |
| JP | 11-29763 | 2/1999 |
| JP | 11-100722 | 4/1999 |
| JP | 11-287790 | 10/1999 |
| WO | WO 99/09238 A1 | 2/1999 |
| WO | WO 00/26301 A1 | 5/2000 |

OTHER PUBLICATIONS

Albright Training Manual Dated Jun. 15, 1999 and titled "The Polyethylene Terephthalte Industry".

Vejrosta, J. et al; Separation of alkali metal carboxybenesuphonate and their 2–hydroxyl esters on Sephadex LH–20 gel, J. Chrmoatography, vol. 109 (1975), pp. 101–106.

Vjrosta, J. et al; Kinetics of esterification of sodium 3,5–dicarboxybenesuphonate with ethylene glycol catalyzed by titanium (IV) and Ti (II) ions, Collect. Czech. Chem. Commun. vol. 43 (1978), pp. 424–433.

*Primary Examiner*—Terressa M. Boykin

(57) ABSTRACT

A process for producing a partially esterified SIPA such as an alkali metal sulfoisophthalic acid in a glycol is disclosed. The partially esterified SIPA in a glycol can be used to copolymerize with oligomer of terephthalic acid dimethyl terephthalate and a glycol. Also disclosed is a process for controlling the color of a dyeable polyester using a phosphorous compound. Further disclosed is a process for producing a dyeable polyester using a nickel or nickel alloy as surface metal or fluoropolymer surface in processing equipment.

38 Claims, No Drawings

SULFOISOPHTHALIC ACID SOLUTION PROCESS THEREWITH

FIELD OF THE INVENTION

This invention relates to a process for producing partially esterified metal salts of sulfoisophthalic acid solutions in a glycol and to a process for producing a polymer comprising repeat units derived from sulfoisophthalic acid or salt thereof or ester thereof, a carbonyl compound, and a glycol in which a phosphorus compound can be used to improve polymer properties.

BACKGROUND OF THE INVENTION

Polyesters are widely used to manufacture textile fibers and bottle resins and can be manufactured by combining a glycol such as ethylene glycol and a carbonyl compound such as dimethyl terephthalate (DMT) or terephthalic acid (TPA). For example, DMT reacts with a glycol such as ethylene glycol to form bis-glycolate ester of terephthalate ("monomer") in the ester exchanger column. The monomer is polymerized by condensation reactions in one or two prepolymerizers and then a final polymerizer or finisher. TPA can be combined with ethylene glycol to form a slurry at 60 to 80° C. followed by injecting the slurry into an esterifier. Linear oligomer with degree of polymerization less than 10 is formed in one or two esterifiers (first and second, if two) at temperatures from 240° C. to 290° C. The oligomer is then polymerized in one or two prepolymerizers and then in a final polymerizer or finisher at temperatures from 250° C. to 300° C.

Additives such as catalysts, stabilizers, delusterants, and toners are often added to the TPA slurry before the esterifier, in the esterifier, or in the oligomer before the prepolymerizer. Commercial polyester processes commonly use antimony compounds as polycondensation catalyst and phosphorous compounds as stabilizers. See generally, Encyclopedia of Chemical Technology, 4th edition, John Wiley, New York, 1994, Volume 10, pages 662–685 and Volume 19, pages 609–653.

However, it is difficult to incorporate a dye material into or onto these polyesters. Therefore, copolymers comprising repeat units derived from terephthalic acid, sulfoisophthalic acid, and glycol are widely used because they can be used to make fibers dyeable by basic dyes or polyester hydrolyzable in water. Such copolymers are referred to as cationic dyeable (CD) polyesters and can be produced by adding small amounts of a sulfonated isophthalate metal salt or its ester such as, for example, sodium dimethylsulfoisophthalate (Na-DMSIP) powder to the ester exchanger of DMT process. Fiber made from CD copolymer gives brilliant shades on dyeing with basic/cationic dyes and also dyes with disperse dyes to deeper shades.

U.S. Pat. No. 5,559,205 discloses a process for adding fully esterified bis(2-hydroxyethyl) sodium 5-sulfoisophthalate (Na-SIPEG) or bis(2-hydroxyethyl) lithium 5-sulfoisophthalate (Li-SIPEG) to the monomer line of DMT process, or oligomer line or the second esterifier of TPA process to make cationic dyeable polyesters.

U.S. Pat. No. 6,075,115 discloses a process for making Na-SIPEG solution and Li-SIPEG solution from sodium 5-sulfoisophthalic acid (Na-SIPA) and to, lithium 5-sulfoisophthalic acid (Li-SIPA) powder. In order to fully esterify the Na-SIPA and Li-SIPA, special titanium catalyst was used, which comprises (1) a titanium compound, a solubility promoter, a phosphorus source, and optionally a solvent, or (2) a titanium compound, a complexing agent, a phosphorus source, and optionally a solvent, a sulfonic acid. The fully esterified Na-SIPEG and LiSIPEG solutions were manufactured by a vendor and then shipped to polyester producers. The solution was then injected into the monomer line of DMT process, or oligomer line or the second esterifier of TPA process to make copolyesters.

These processes have several disadvantages including (1) high cost of 20% Na-SIPEG solution and 20% Li-SIPEG solution, because a separate facility is required to make these solutions from Na-SIPA or Li-SIPA powder and glycol; (2) high transportation cost for the 20% solutions; (3) high investment cost to build a heated storage tank, pump, and piping system for the 20% solutions; (4) cationic dyeable polyester producers cannot control the properties of the solutions such as DEG (diethylene glycol), acidity, carboxyl groups, and concentration; and (5) a tendency to form dimer and/or trimer in the solutions.

Therefore, there is a need to develop a process to produce a partially esterified Na-SIPA solution and Li-SIPA solution that is more stable and less likely to form solids when cooled to room temperature, especially at high concentrations. An advantage of the invention is that the partially esterified Na-SIPA and Li-SIPA solutions can be made immediately before it is used in producing polyester thereby significantly reducing manufacturing and transportation cost. Another advantage is that the unesterified carboxyl groups partially accelerate the polycondensation reaction thereby improving productivity. Also an advantage is that the properties of the solution can be better controlled. A further advantage is that less dimer, trimer, or tetramer is produced rendering a more stable Na-SIPA or Li-SIPA solution and more uniform basic dye site distribution in the resulting polymer.

Additionally, it is well known that phosphoric acid is commonly used to control the discoloration of polyester homopolymer, but phosphoric acid does not improve the color of copolymer derived from terephthalic acid and sulfoisophthalic acid. Thus, there is also a need to develop a process using a nonacidic phosphorus compound to improve the color of dyeable polyester.

Furthermore, stainless steel or carbon steel is commonly used as surface metal of process equipment, such as heat exchanger, for commercial production of a polymer having repeat units derived from an alkali metal SIPA. An alkali metal SIPA prepolymer formed during the production was found to stick on the metal surface of the process equipment degrading or carbonizing into black solids and, subsequently, resulting in process plugging, which requires shutdown every 1 to 4 months to clean the plugged tubes. Therefore, it is also a need to identify process equipment for producing a polymer having repeat units derived from an alkali metal SIPA.

SUMMARY OF THE INVENTION

A process that can be used for producing a partially esterified SIPA in a first glycol is disclosed. The process comprises contacting a SIPA to produce a mixture and heating the mixture under a condition sufficient to partially esterify the SIPA wherein the mixture optionally comprises a catalyst.

Also disclosed is a process that can be used for controlling the color of a dyeable polyester. The process comprises contacting, optionally in the presence of a phosphorus compound and/or a catalyst, a SIPA or partially esterified SIPA with either (a) a polymerization mixture comprising a carbonyl compound and a second glycol or (b) an oligomer derived from a carbonyl and a second glycol.

Further disclosed is a process for producing a dyeable polyester. The process comprises contacting, optionally in the presence of a phosphorus compound and/or a catalyst, a SIPA or partially esterified SIPA with either (a) a polymerization mixture comprising a carbonyl compound and a second glycol or (b) an oligomer derived from a carbonyl and a second glycol wherein the process is carried out in a vessel or process equipment having nickel or a nickel alloy as surface metal or fluoropolymer as a surface.

DETAILED DESCRIPTION OF THE INVENTION

The acronym "SIPA" used herein can have the formula of $(RO(O)C)_2ArS(O)_2OM$ in which each R can be the same or different and is hydrogen or an alkyl group containing 1 to about 6 carbon atoms or hydroxyalkyl group containing 1 to 6 carbon atoms; Ar is a phenylene group; and M is hydrogen, an alkali metal, an alkaline earth metal, quaternary ammonium or phosphonium, or combinations of two or more thereof. The preferred M is an alkali metal such as lithium or sodium. Accordingly, SIPA, unless otherwise specifically indicated, can also include those that are partially or fully esterified.

As such, "SIPA", unless otherwise specifically indicated, can collectively refer to 5-sulfoisophthalic acid, alkali metal salt of 5-sulfoisophthalic acid, an ester of 5-sulfoisophthalic acid, an ester of alkali metal salt of 5-sulfoisophthalic acid, or combinations of two or more thereof. For example, Na-SIPA and Li-SIPA are referred to, because they are specifically indicated, sodium 5-sulfoisophthlalic acid and lithium 5-sulfoisophthlalic acid, respectively. Also, for example, specifically indicated Na-DMSIP refers to sodium dimethyl 5-sulfoisophthalate. Further, for example, specifically indicated Na-SIPEG and Li-SIPEG refers to fully esterified sodium 5-sulfoisophthalate and fully esterified lithium 5-sulfoisophthalate, respectively, in ethylene glycol; specifically indicated Na-SIPPG and Li-SIPPG refers to fully esterified sodium 5-sulfoisophthalate and fully esterified lithium 5-sulfoisophthalate, respectively, in propylene glycol (1,3-propanediol).

Similarly, the term "partially esterified SIPA" used herein, unless otherwise specifically indicated, refers to partially esterified 5-sulfoisophthalic acid, partially esterified alkali metal salt of 5-sulfoisophthalic acid, an ester of partially esterified 5-sulfoisophthalic acid, an ester of partially esterified alkali metal salt of 5-sulfoisophthalic acid, or combinations of two or more thereof. The term "partially esterified" used herein, unless otherwise indicated, refers to esterifcation of about 30% to about 99%, preferably about 50% to about 99%, and most preferably 80% to 95%, by mole, of the total carboxyl groups of SIPA. Any alkali metal SIPA powder can be used. The preferred alkali metal SIPA is Li-SIPA, Na-SIPA, or combinations thereof.

Examples of SIPA include, but are not limited to, 5-sulfoisophthalic acid; alkali metal salt of 5-sulfoisophthalic acid such as sodium 5-sulfoisophthalic acid (Na-SIPA), lithium 5-sulfoisophthalic acid (Li-SIPA); a mono- or di-ester of 5-sulfoisophthalic acid; a mono- or di-ester of alkali metal salt of 5-sulfoisophthalic acid such as bis(2-hydroxyethyl) sodium 5-sulfoisophthalate (Na-SIPEG), bis(2-hydroxyethyl) lithium 5-sulfoisophthalate (Li-SIPEG), sodium dimethyl 5-sulfoisophthalate (Na-DMSIP), lithium dimethyl 5-sulfoisophthalate (Li-DMSIP), bis(3-hydroxypropyl) sodium 5-sulfoisophthalate (Na-SIPPG), bis(3-hydroxypropyl) lithium 5-sulfoisophthalate (Li-SIPPG), and combinations of two or more thereof.

According to the invention, the term "glycol" is interchangeable with "alcohol". Any glycol that can esterify SIPA can be used as the first glycol of the invention. The preferred glycol can have 1 to about 10, preferably 1 to about 8, and most preferably 1 to 4 carbon atoms per molecule such as, for example, an alkylene glycol, a polyalkylene glycol, polyoxyalkylene glycol, or combinations thereof. Examples of suitable glycols include, but are not limited to, ethylene glycol, propylene glycol, isopropylene glycol, butylene glycol, 1-methyl propylene glycol, pentylene glycol, diethylene glycol, triethylene glycol, polyethylene glycols, polyoxyethylene glycols, polyoxypropylene glycols, polyoxybutylene glycols, and combinations of two or more thereof. The presently most preferred glycol is an alkylene glycol such as ethylene glycol or 1,3-propanediol for the polyester produced therefrom has a wide range of industrial applications.

An alkali metal SIPA can be combined with a glycol in any suitable manner and in any suitable container, vessel, or reactor to produce an alkali metal SIPA-glycol mixture. The quantity of the metal SIPA can be any quantity so long as the quantity can produce a desired partially esterified alkali metal SIPA. Generally, based on total weight of the alkali metal SIPA-glycol mixture, the metal SIPA can be present in the range of about 5% to about 70%, preferably about 10% to about 50%, and most preferably 20% to about 40% by weight.

A metal salt such as sodium acetate or lithium acetate dihydrate can be added to the alkali metal SIPA-glycol mixture in the amount of about 0.2 to about 200 g, preferably 2 to 20 g, per kg alkali metal SIPA to control the formation of diethylene glycol. The metal SIPA-glycol mixture in slurry form can be heated at about 60° C. to about 250° C., preferably about 100° C. to about 200° C., and most preferably 140° C. to 190° C. for at least about 5 minutes, preferably about 1 to about 4 hours. Water is a by-product. Water and glycol vapor can be condensed in a condenser or discharged in the air, or flow to a water separation column. Thereafter, the resulting solution can be further heated at the same or lower temperature. The solution, whether further heated or not, can be directly used in a process for producing polyester such as, for example, being injected into the monomer line or prepolymerizer of DMT process, or the oligomer line or the second esterifier or prepolymerizer of TPA process discussed in the BACKGROUND OF THE INVENTION.

Optionally, a catalyst such as a titanium-containing compound can be introduced into the metal SIPA-glycol mixture slurry (before, during or after the slurry is heated) or solution (while solution is being formed or continually heated or cooled). If a catalyst is introduced before or during the heating, it can accelerate the esterification reaction. The catalyst can also accelerate polycondensation reaction unless it is deactivated by an inhibitor. Other catalysts such as cobalt, antimony, manganese, or zinc catalyst commonly employed in the manufacture of polyester can also be used. The description of these catalysts is omitted herein because such catalyst is well known to one skilled in the art.

The preferred titanium compounds used in the process are organic titanium compounds such as, for example, titanium tetrahydrocarbyloxides, also referred to as tetraalkyl titanates herein for they are readily available and effective. Examples of suitable titanium tetrahydrocarbyloxides include those having the formula of $Ti(OR^1)_4$ where each $R^1$ is individually selected from an alkyl, cycloalkyl, alkaryl, hydrocarbyl radical containing from 1 to about 30, preferably 2 to about 18, and most preferably 2 to 12 carbon atoms per radical and each $R^1$ can be the same or different. Titanium tetrahydrocarbyloxides in which the hydrocarboxyl group contains from 2 to about 12 carbon atoms per radical which is a linear or branched alkyl radical are most preferred because they are relatively inexpensive, more readily available, and effective in forming the solution. Suitable titanium tetrahydrocarbyloxides include, but are not limited to, titanium tetraethoxide, titanium tetrapropoxide, titanium tetraisopropoxide, titanium tetra-n-butoxide, titanium tetrahexoxide, titanium tetra 2-ethylhexoxide, titanium tetraoctoxide, and combinations of two or more thereof. The titanium tetrahydrocarbyloxides are well known to one skilled in the art. See, for example, U.S. Pat. Nos. 6,066,714 and 6,166,170, the description of which is incorporated herein by reference. Examples of commercially available organic titanium compounds include, but are not limited to, TYZOR® TPT and TYZOR® TBT (tetra isopropyl titanate and tetra n-butyl titanate, respectively) available from E. I. du Pont de Nemours and Company, Wilmington, Del., U.S.A.

A titanium-containing composition can be produced by any means known to one skilled in the art such as those disclosed in U.S. Pat. Nos. 6,066,714 and 6,166,170 discussed above and description of which is omitted herein for the interest of brevity.

A titanium-containing composition can also include, but are not limited to, a titanium solution made from a titanium compound disclosed above and a glycol disclosed above, in the presence of a phosphorus compound. Any phosphorus compound that can stabilize a titanium-glycol solution, i.e., can prevent the solution from gelling or precipitation, can be used. Any phosphorus compound that, when used with a polyester catalyst, produces polyester having low yellowness, as compared to a polyester produced from a catalyst without such phosphorus compound, can be used. Examples of suitable phosphorus compounds include, but are not limited to, a polyphosphoric acid or a salt thereof, a phosphonate ester, a pyrophosphoric acid or salt thereof, a pyrophosphorous acid or salt thereof, and combinations of two or more thereof. The polyphosphoric acid can have the formula of $H_{n+2}P_nO_{3n+1}$ in which n is $\geq 2$. The phosphonate ester can have the formula of $(R^2O)_2P(O)ZCO_2R^2$ in which each $R^2$ can be the same or different and can be independently H, $C_{1-4}$ alkyl, or combinations thereof; and Z is $C_{1-5}$ alkylene, $C_{1-5}$ alkylidene, or combinations thereof, di(polyoxyethylene)hydroxymethyl phosphonate, and combinations of two or more thereof. The salt can be an alkali metal salt, alkaline earth metal salt, ammonium salt, or combinations of two or more thereof.

Illustrative examples of suitable phosphorus compounds include, but are not limited to, potassium tripolyphosphate, sodium tripolyphosphate, potassium tetra phosphate, sodium pentapolyphosphate, sodium hexapolyphosphate, potassium pyrophosphate, potassium pyrophosphite, sodium pyrophosphate, sodium pyrophosphate decahydrate, sodium pyrophosphite, ethyl phosphonate, propyl phosphonate, hydroxymethyl phosphonate, di(polyoxyethylene) hydroxymethyl phosphonate, methylphosphonoacetate, ethyl methylphosphonoacetate, methyl ethylphosphonoacetate, ethyl ethylphosphonoacetate, propyl dimethylphosphonoacetate, methyl diethylphosphonoacetate, triethyl phosphonoacetate, or combinations of two or more thereof.

For example, a titanium-containing catalyst can contain a salt of a polyphosphoric acid disclosed above, having 0.001% to 10% titanium, 50% to 99.999% glycol, and 0% to 50% water, all weight % in which the molar ratio of phosphorus to titanium is about 0.001:1 to 10:1.

The catalyst can further comprise a cocatalyst. Examples of cocatalysts include, but are not limited to, cobalt/aluminum catalysts, antimony compounds, and combinations thereof. The cobalt/aluminum catalyst comprises a cobalt salt and an aluminum compound in which the mole ratio of aluminum to cobalt is in the range of from 0.25:1 to 16:1. The cobalt/aluminum catalyst is disclosed in the U.S. Pat. No. 5,674,801, disclosure of which is incorporated herein by reference.

Optionally, de-foaming agent such as, for example, polydimethylsiloxane (or its emulsion or solution) can be introduced into the metal SIPA-glycol mixture slurry (before, during or after the slurry is heated) or solution (while solution is being formed or continually heated or cooled). The de-foaming agent can reduce surface tension thereby preventing the slurry or solution from foaming and stabilizing the subsequent polycondensation process, if the solution is used for producing polyester. Because the de-foaming agents are so well known to one skilled in the art, the description is omitted herein in the interest of brevity.

According to another embodiment of the invention, a process comprises contacting, optionally in the presence a phosphorus compound and/or a catalyst, either (a) a SIPA or partially esterified SIPA with a polymerization mixture comprising a carbonyl compound and a second glycol or (b) a SIPA or partially esterified SIPA with an oligomer derived from a carbonyl and a second glycol.

The phosphorus compound, catalyst, and partially esterified SIPA can be the same as those disclosed above and the disclosures of which are incorporated here. The second glycol can be the same or different from the first glycol and can include those disclosed above for the first glycol. The presently preferred second glycols are ethylene glycol and 1,3-propanediol.

According to the invention, the phosphorus compound can be present in the process before, during, or after a carbonyl compound or ester thereof is esterified or transesterified. Similarly, it can be present before, during, or after the polycondensation stage. The phosphorus compound can be used to inhibit the catalytic activity of a titanium-containing catalyst or other catalysts or trace elements such as manganese, cobalt, zinc, aluminum, iron, lead, silicon, to reduce the discoloration of polyester produced using a titanium-containing catalyst or other catalysts or trace elements, or both. The phosphorus compound can be mixed with the catalyst, such as titanium, antimony, manganese, zinc, before the catalyst is introduced to the polyester reaction process. Alternatively, the phosphorous compound can be introduced to the process separately before or after the catalyst is introduced.

For example, in a TPA process, a titanium catalyst, alone or with other catalysts such as antimony can be used as polycondensation catalyst for an oligomer. Alternatively, a titanium-containing catalyst can be present in the ester exchanger to accelerate transesterification reaction or in the esterifier to accelerate the esterification reaction. Generally, titanium-containing catalyst is more active in polycondensation reaction than in esterification or transesterification. The proper level of titanium-containing catalyst for esterification or transesterification can be an excess level for polycondensation. When titanium-containing catalyst presented in the esterifier or ester exchanger (transesterifier) is an excess for polycondensation, or when polycondensation is intended with a non titanium-containing catalyst such as antimony, part of or all of the titanium catalyst is preferably deactivated or inhibited after esterification or transesterification with phosphoric acid or the phosphorus compounds (change only if you exclude phosphoric acid above) disclosed above, to avoid discoloration of the polymer.

The titanium-containing catalyst present in the polymer can cause increased degradation and yellowness in the future processing. Part of or all of the titanium catalyst can be deactivated or inhibited after polymerization with a phosphorus compound disclosed, to avoid discoloration of the polymer.

Similarly, when manganese, zinc, cobalt, aluminum, silicon, or other catalysts are used as esterification or transesterification catalyst and titanium-containing catalyst is used as polycondensation catalyst, these catalysts can be deactivated by the presence of a phosphorous compound disclosed above.

Any carbonyl compound, which when combined with a glycol, can produce a polyester can be used. Such carbonyl compounds include, but are not limited to, acids, esters, amides, acid anhydrides, acid halides, salts of carboxylic acid oligomers or polymers having repeat units derived from an acid, or combinations of two or more thereof. The presently preferred acid is an organic acid such as a carboxylic acid or salt thereof. The oligomer of a carbonyl compound such as TPA and glycol generally has a total of about 2 to about 100, preferably from about 2 to about 20 repeat units derived from the carbonyl compound and glycol.

The organic acid or ester thereof can have the formula of $R^3COOR^3$ in which each $R^3$ independently can be (1) hydrogen, (2) hydrocarboxyl radical having a carboxylic acid group at the terminus, or (3) hydrocarbyl radical in which each radical has 1 to about 30, preferably about 3 to about 15 carbon atoms per radical which can be alkyl, alkenyl, aryl, alkaryl, aralkyl radical, or combinations of two or more thereof. The presently preferred organic acid or ester thereof has the formula of $R^3O_2CACO_2R^3$ in which A is an alkylene group, an arylene group, alkenylene group, or combinations of two or more thereof and $R^2$ is the same as above. Each A has about 2 to about 30, preferably about 3 to about 25, more preferably about 4 to about 20, and most preferably 4 to 15 carbon atoms per group. Examples of suitable organic acids include, but are not limited to, terephthalic acid, isophthalica acid, napthalic acid, succinic acid, adipic acid, phthalic acid, glutaric acid, oxalic acid, maleic acid, and combinations of two or more thereof. Examples of suitable esters include, but are not limited to, dimethyl adipate, dimethyl phthalate, dimethyl terephthalate, dimethyl glutarate, and combinations of two or more thereof.

The presently preferred organic diacid is terephthalic acid or its ester dimethyl terephthalate because the dyeable polyesters produced therefrom have a wide range of industrial applications.

The contacting of the carbonyl compound and glycol in the presence of the catalyst can be carried out by any suitable means.

Any suitable condition to effect the production of a polyester can include a temperature in the range of from about 150° C. to about 500° C., preferably about 200° C. to about 400° C., and most preferably 250° C. to 300° C. under a pressure in the range of from about 0.001 to about 1 atmosphere for a time period of from about 0.2 to about 20, preferably about 0.3 to about 15, and most preferably 0.5 to 10 hours.

The molar ratio of the glycol to carbonyl compound can be any ratio so long as the ratio can effect the production of an ester or polyester. Generally the ratio can be in the range of from about 1:1 to about 10:1, preferably about 1:1 to about 5:1, and most preferably 1:1 to 4:1. The CD polyester produced by the invention process can comprise about 1 to about 200 parts per million by weight (ppm) of titanium and about 1 to about 200 ppm, preferably about 5 to about 100 ppm, of phosphorus. If two or more carbonyl compounds are employed, the molar ratio of the second or third carbonyl compound to the first carbonyl compound can each be in the range of from about 0.0001:1 to about 1:1. For example, a dyeable polyester can comprise 85 mole % to 99.9 mole % of repeat units derived from terephthalic acid or terephthalate and 0.1 mole % to 15 mole % of repeat units derived from sodium 5-sulfoisophthalic acid or lithium 5-sulfoisophthalic acid.

As disclosed above, the catalyst can be a cobalt, antimony, manganese, or zinc catalyst commonly employed in the manufacture of polyester. A preferred antimony compound can be any antimony compound that is substantially soluble in a solvent disclosed above. Examples of suitable antimony compounds include, but are not limited to, antimony oxides, antimony acetate, antimony hydroxides, antimony halides, antimony sulfides, antimony carboxylates, antimony ethers, antimony glycolates, antimony nitrates, antimony sulfates, antimony phosphates, and combinations of two or more thereof. The catalyst, expressed as element Co, Sb, Mn, Zn, or Ti, Al, Si, can be present in the range of about 0.001 to about 30,000 ppm of the medium comprising the carbonyl compound and glycol, preferably about 0.1 to about 1,000 ppm, and most preferably 1 to 100 ppm by weight. A cocatalyst, if present, can be in the range of from about 0.01 to about 1,000 ppm of the reaction medium.

The invention process can also be carried out using any of the conventional melt or solid state techniques and in the presence or absence of a toner compound to reduce the color of a polyester produced. Example of toner compounds include, but are not limited to, cobalt aluminate, cobalt acetate, Carbazole violet (commercially available from Hoechst-Celanese, Coventry, R.I., U.S.A., or from Sun Chemical Corp, Cincinnati, Ohio, U.S.A.), Estofil Blue S-RLS® and Solvent Blue 45™ (from Sandoz Chemicals, Charlotte, N.C., U.S.A), CuPc Blue (from Sun Chemical Corp, Cincinnati, Ohio, U.S.A.). These toner compounds are well known to one skilled in the art and the description of which is omitted herein. The toner compound can be used with the catalyst disclosed herein in the amount of about 0.1 ppm to 1000 ppm, preferably about 1 ppm to about 100 ppm, based on the weight of polyester produced.

The invention process can also be carried out using any of the conventional melt or solid state techniques and in the presence or absence of an optical brightening compound to reduce the yellowness of the polyester produced. Example of optical brightening compounds include, but are not limit to, 7-naphthotriazinyl-3-phenylcoumarin (commercial name "Leucopure EGM", from Sandoz Chemicals, Charlotte, N.C., U.S.A.), 4,4'-bis(2-benzoxazolyl) stilbene (commercial name "Eastobrite", from Eastman Chemical, Kingsport, Tenn., U.S.A). These optical brightening compounds are well known to one skilled in the art and the description of which is omitted herein. The optical brightening compound can be used with the catalyst disclosed herein in the amount of about 0.1 ppm to 10000 ppm, preferably about 1 ppm to about 1000 ppm, based on the weight of polyester produced.

According to a further embodiment of the invention, a process for producing a dyeable polyester is provided. The process comprises contacting either (a) a SIPA or partially esterified SIPA with a polymerization mixture comprising a carbonyl compound and a second glycol or (b) a SIPA or partially esterified SIPA with an oligomer derived from a carbonyl and a second glycol. The process is carried out in a vessel (or container or reactor) having nickel or a nickel alloy as surface metal or fluoropolymer as surface and can be carried out in the presence of a catalytic amount of a catalyst and a phosphorus compound. The glycol, catalyst, phosphorus compound, carbonyl compound, partially esterified alkali metal 5-sulfoisophthalic acid, and process conditions can be the same as those disclosed above.

Generally a nickel-surfaced vessel or process equipment can comprise nickel metal, Ni 99 to 100%. A nickel alloy-surfaced vessel or process equipment can comprise by weight: Ni, 25 to 85%; Mo, 0 to 30%; Fe, 0 to 50%; Cu, 0 to 33%; Cr, 0 to 24%; Si, 0 to 10%; and other elements such as Mn, Ti, Al, Co, W, Cb, V, Ta, P, S, 0 to 5% each. The following are examples of commercially available nickel and nickel alloys commercially available in the U.S.A. Composition is by weight, trace metals of less than 0.9% were not listed in composition. Nickel 200 and Nickel 201 (Ni 99.5%), Hastelloy B (Ni 61.0%, Mo 28.0%, Fe 5.5%, Co 2.5%, Cr 1.0%, Si 1.0%, Mn 1.0%), Hastelloy D (Ni 82.0%, Si 9.25%, Cu 3.0%, Fe 2.0%, Co 1.5%, Cr 1.0%, Mn 0.9%, Co 1.25%, Cb 2.1%), Hastelloy C-276 (Ni 57.0%, Mo 16.0%, Fe 5.5%, W 3.75%, Co 1.25%), Monel 400 (Ni 66.5, Cu 31.5, Fe 1.25%, Mn 1.0%), Monel K-500 (Ni 66.5%, Cu 29.5%, Fe 1.0%, Al 2.73%), Carpenter 20Cb-3 (Ni 34.0%, Cr 20.0%, Cu 3.5%, Mo 2.5%, Mn 1.0%), Inconel 600 (Ni 76.0%, Cr 15.5%, Fe 8.0%,), Incoloy 625 (Ni 61.0%, Cr 21.5%, Mo 9.0%, Fe 2.5%, Cb 3.65%), Incoloy 825 (Ni 42.0%, Fe 30.0%, Cr 21.5%, Mo 3.0%, Cu 2.25%, Ti 0.9%). It is preferred the nickel or nickel alloy surface be polished.

Fluoropolymer refers to a fluorinated polymer or copolymer. Any fluoropolymer can be used. Examples of commercially available fluoropolymers include, but are not limited to, polytetrafluoroethylene (Teflon® PTFE), perfluroalkoxy copolymer (Teflon® PFA), perfluoro ethylene-propylene copolymer (Teflon® FEP), ethylene-tetrafluoroethylene (Tefzel® EFTE), perfluoropolyether such as Krytox™, Kalrez®, Viton®, poly-vinylidine fluoride, fluorosilicones, and combinations of two or more thereof. These fluoropolymers are available from E. I. du Pont de Nemours and Company, Wilmington, Del., U.S.A.

EXAMPLES

The following examples are included to further illustrate the invention and are not to be construed as to unduly limit the scope of the invention.

The number of carboxyl groups COOH before esterification was calculated from concentration and chemical formula. The number of carboxyl groups COOH in the partially esterified SIPA solution was determined as follows. A weighed specimen is dissolved in o-cresol, diluted with chloroform and titrated with methanolic potassium hydroxide to a bromophenol blue end point. The end point was determined calorimetrically at 600 nm using a recording titrator.

Water was determined by the Karl Fisher method. Water was converted stochimetrically in the presence of sulfur dioxide, methanol and suitable base of addition iodine. The titration was followed by a two-pin platinum electrode having a current source applied to its poles. The voltage measured at the polarized electrode pins was used by the control as an input signal. When the last trace of water was titrated out, voltage dropped to virtually zero. The electrodes were then depolarized by the iodine now present; the small electrical current oxides iodine at one electrode and reduces the amount of iodine at the other electrode.

Diethylene glycol (DEG) in the partially esterified SIPA solution was analyzed in the same way as DEG in polymer, which requires depolymerization. The samples were treated with 2-aminoethanol (2AE) containing benzyl alcohol (BA) as an internal standard. The reaction mixture was diluted with isopropyl alcohol and injected into a gas chromatograph. The ratio of the areas of the DEG and BA peaks, corrected for the sample weight, was translated by a calibration factor into weight percent DEG. Dipropylene glycol (DPG) was analyzed similarly as DEG.

In the intrinsic viscosity (I.V.) analysis, weighed polymer sample was dissolved in hexafluoroisopropanol (HFIP) to make 4.75% solution. The drop time of the solution at 25° C. was measured using a constant volume viscometer in an Octavisc® auto viscometer system. Color of the resulting oligomer and any polymer produced therefrom was measured in terms of the L-value and b-value, using a Hunter color instrument.

In boil off shrinkage analysis, a filament of about 30 cm long was placed in boiling water at 100° C. for 30 minutes, the length before and after that was measured. In dry heat shrinkage, a filament of about 30 cm long was placed in an oven at 160° C. for 30 minutes, the length before and after that was measured.

The tenacity and elongation were from stress-strain curve measured by Model 1122 or 1123 Instron. Instron is a commercial testing equipment equipped with a strain gauge to measure force precisely, a "crosshead" that moves at a controllable constant speed, a chart recorder to record a graph of force vs. crosshead movement, and provision for interfacing with a computer to read and process force and motion data.

Example 1

This example illustrates the preparation of partially esterified Na-SIPA solution in ethylene glycol.

Titanium catalyst solution was prepared as follows. Ethylene glycol (EG; 136 g) and potassium tripolyphosphate (KTPP; 5 g; from FMC Corp., Philadelphia, Pa., U.S.A.) were charged to a glass beaker and agitated 1 hour at 60° C. to produce a clear solution, to which was added 19 g of Tetraisopropyl titanate (TPT; from DuPont de Nemours & Company, Wilmington, Del., U.S.A.) to produce about 160 g of a clear solution containing 2% Ti with P/Ti molar ratio 0.5.

EG (418.2 g) and sodium 5-sulfoisophthalic acid (Na-SIPA; 180 g; from Eastman Chemical, Kingsport, Tenn., U.S.A.; active ingredient 98% by weight) were added in a kettle, which had been nitrogen-purged and had a small opening to remove water vapor, to produce a slurry. The titanium catalyst described above (Ti 2.0% by weight, P/Ti molar ratio 0.5; 1.8 g) was added to this slurry.

It took 80 minutes to heat the agitated slurry slowly to 180° C. Na-SIPA was completely dissolved when the temperature reached about 140° C. A sample was taken when the temperature reached 180° C.. This clear solution sample did not solidify when cooled. Carboxyl groups COOH were analyzed to be 249 meq/kg (89.2% COOH esterified), diethylene glycol (DEG) 0.83%, water 2.15%.

After heating at 180° C. for 1 hour, a sample was taken, the sample remained clear when cooled to room temperature. Carboxyl groups COOH were analyzed to be 95 meq/kg (95.9% COOH esterified), diethylene glycol (DEG) 3.56%, water 1.77%.

After heating at 180° C. for 2 hours, a sample was taken, the sample remained clear when cooled to room temperature. Carboxyl groups COOH were analyzed to be 86 meq/kg (96.3% COOH esterified), diethylene glycol (DEG) 5.73%, water 1.51%.

Example 2

This example shows the preparation of partially esterified Li-SIPA solution in 1,3-propanediol.

1,3-propanediol (419.8 g) and lithium 5-sulfoisophthalic acid (Li-SIPA; 180 g; from Eastman Chemical, Kingsport, Tenn., U.S.A.; active ingredient 91% by weight) were mixed as in EXAMPLE 1 to produce a slurry. TPT (0.2136 g) was added to this slurry. It took 40 minutes to heat the agitated slurry to 180° C. Li-SIPA was completely dissolved when the temperature reached about 160° C. A sample was taken when it reached 180° C. This yellowish clear solution sample did not solidify when cooled. Carboxyl groups COOH were analyzed to be 293 meq/kg (87.1% COOH esterified), dipropylene glycol (DPG) 10.1%, water 2.47%.

After heating at 180° C. for 1 hour, a sample was taken, the sample remained as yellowish clear solution when cooled to room temperature. Carboxyl groups COOH were analyzed to be 68 meq/kg (97.0% COOH esterified), dipropylene glycol (DPG) 17.5%. DPG formation in the solution can be controlled by adding lithium acetate dihydrate as Example 8.

Example 3

This example shows a mass balance of an invention solution due to evaporation of water and glycol.

EG (424.2 g), Na-SIPA (173.2 g; from Eastman Chemical), sodium acetate (0.866 g), and titanium catalyst solution described in Example 1 (Ti 2.0%, P/Ti molar ratio 0.5; 1.732 g) were added to a kettle. Total weight of the mixture was 600 grams. The kettle was purged with nitrogen, the vapor was condensed in a two-stage condensing system with dry ice.

Twenty minutes after heating started from about 25° C. (room temperature), the mixture began to boil at 176° C., it became clear at this time. It reached 180° C. in 40 minutes from the start of boiling, boiling stopped when temperature reached 180° C., total boiling time was about 40 minutes. The solution was maintained at 180° C. for 1 hour after boiling stopped. Then the solution was cooled to room temperature by stopping heating. The cooled solution was clear golden brown.

The weight of solution in the kettle was 565.6 grams, the condensed vapor was 17.55 grams. Analysis of the solution showed: Carboxyl groups, 141 meq/kg (93.7% of IPA COOH esterified); DEG, 1.84%; water, 1.51%; Brookfield viscosity at 20° C., 306 cps; specific gravity, 1.22 g/ml.

Example 4

Examples 4 and 5 illustrate a continuous polymerization process to produce polyester copolymer 45.4 kg/hour in a pilot plant. The polyester esterification, polycondensation, and spinning process are well known to one skilled in the art, only a brief description is provided herein.

Bis(2-hydroxyethyl) sodium 5-sulfoisophthalate (Na-SIPEG) solution was produced by DuPont de Nemours & Company, Wilmington, Del. from sodium dimethyl 5-sulfoisophthalate (Na-DMSIPA) through a transesterification process with manganese acetate catalyst. The Na-SIPEG solution contained 20% Na-SIPEG and 80% ethylene glycol by weight.

TPA slurry with ethylene glycol to TPA molar ratio 2.2 was injected into a recirculating esterifier, only virgin ethylene glycol was used to make the slurry.

The esterifier slurry inlet temperature was 282° C. and heat exchanger outlet temperature was 284° C.

Na-SIPEG solution was injected into oligomer. Sodium acetate in ethylene glycol solution containing sodium acetate 3% by weight was injected into oligomer at a rate of 200 ppm Na in polymer by weight. Anatase $TiO_2$ in ethylene glycol slurry containing 20% $TiO_2$ was injected into oligomer at a rate of 0.035% $TiO_2$ in polymer by weight. No catalyst was injected. No phosphorous compound was injected.

The first prepolymerizer ("flasher") was 265° C. at vacuum 110 mm Hg (14.67 kPa), the second prepolymerizer was 275° C. at vacuum 30 mm Hg (4.0 kPa), the final polymerizer ("finisher") temperature was 280° C. Finisher pressure was controlled by an online melt viscosity instrument which measured polymer molecular weight. In this example, the average of finisher pressure was 1.98 mm Hg (0.26 kPa). Polymer temperature in the transfer line from finisher to spinning machine was 280° C.

Laboratory analysis indicated polymer intrinsic viscosity was 0.556. This polymer contained 1.99% Na-SIPA by mole, 24 ppm manganese by weight which was from Na-SIPEG solution, phosphorous 4.1 ppm by weight, no antimony, 0.039% $TiO_2$ by weight, 1.83% DEG by weight, and 24 meq/kg carboxyl group.

Partially oriented yarn (POY) of 68 filaments of round cross section with tow denier 245 g/9000 m was wound to a tube at 2917 meters/min. Eight tubes were wound simultaneously, the wound tubes were taken off from the winding machine hourly. Polymer flow rate in the spinning pack was about 39.5 kg/hour, which was controlled by a meter pump and adjusted to obtain the desired denier. The ballast polymer which did not flow into spinning machine was pumped to a waste drum. The POY had physical properties shown in Table 1. This POY was textured and dyed with cationic dyes.

Example 5

The process in Example 5 was the same as Example 4. Phosphoric acid ($H_3PO_4$) in ethylene glycol solution containing $H_3PO_4$ 0.5% by weight was injected into oligomer line at a rate of 10 ppm P in polymer.

Laboratory analysis indicated polymer intrinsic viscosity was 0.538. This polymer contained 2.00% Na-SIPA by mole, 24 ppm manganese by weight, phosphorous 12.4 ppm by weight, no antimony, 0.033% $TiO_2$ by weight, 1.85% DEG by weight, and 20 meq/kg carboxyl group. The melt polymer was spun to POY (partially oriented yarn; 245 denier 68 filaments) having the properties shown in Table 1. This POY was textured and dyed with cationic dyes.

This example indicates phosphoric acid does not improve the L color (brightness) and b color (yellowness) of copolymer from TPA process.

Example 6

This example illustrates a continuous polymerization process for polyester copolymer with a polymer flow rate of 45.4 kg/hour in a pilot plant. Partially esterified Na-SIPA solution was injected into TPA oligomer. Phosphonate ester improved polymer b color (lower yellowness). The esterification, polycondensation, and spinning process were similar to Example 4.

EG (160 kg), Na-SIPA (from Taoka Chemical Co., Osaka, Japan; 40 kg), and sodium acetate (140 g) were charged to a mix tank, which had nitrogen purge and an open discharge port to remove water vapor, to produce a slurry. It took 105 minutes to heat the agitated slurry from 58° C. to 180° C. Na-SIPA was completely dissolved at about 100° C.. After heating at 182° C. for 3 hours, heating was stopped. Sample was taken 6 hours later at 124° C. Carboxyl groups COOH were analyzed to be 164 meq/kg (89.5% COOH esterified), DEG 0.94%, water 1.54%, Brookfield viscosity 80 cp at 20° C. The partially esterified Na-SIPA solution sample remained clear when cooled to room temperature.

Polydimethylsiloxane (80 g; from Dow Chemical, Midland, Mich., U.S.A.; viscosity 500 cSt) was added to the solution in the mix tank, while being agitated, after the heating. The resulting solution was pumped to the feed tank, where the solution temperature decreased to 60–80° C., before it was injected into TPA oligomer to make copolymer. Sodium acetate was injected to reduce DEG in polymer at a rate of 200 ppm Na in polymer. Triethyl phosphonoacetate (TEPA; from Albright & Wilson America, Richmond, Va., U.S.A.) in ethylene glycol solution containing TEPA 1.145% was injected into oligomer line at a rate of 30 ppm P in polymer. Antimony glycolate in ethylene glycol solution containing Sb 1% by weight was injected into oligomer line at a rate of 100 ppm Sb in polymer.

TPA esterifier temperature was 284° C., only virgin glycol was used to make TPA slurry. The first prepolymerizer ("flasher") was 265° C. at vacuum 120 mm Hg (16.0 kPa), the second prepolymerizer was 280° C. at vacuum 40 mm Hg (5.33 kPa), the final polymerizer ("finisher") temperature was 285° C. The average of finisher pressure was 5.34 mm Hg (0.71 kPa). Polymer temperature in the transfer line from finisher to spinning machine was 285° C.

Laboratory analysis showed: The polymer had intrinsic viscosity 0.544, contained 2.18% Na-SIPA by mole, 120 ppm antimony, 0.030% $TiO_2$, 24 ppm phosphorus, 2.30% DEG, and 22 meq/kg carboxyl group. The melt polymer was spun to POY (245 denier 68 filaments) having the properties shown in Table 1. This POY was textured and dyed with cationic dyes.

Compared with Examples 4 and 5 which also used virgin glycol to make TPA slurry, the partially esterified Na-SIPA solution and phosphonate ester TEPA in this example reduced polymer b color 1.4 units (less yellow, desirable).

Example 7

This example shows a continuous polymerization process to make semi-dull polymer 50 kg/hour in a pilot plant. Higher concentration of partially esterified Na-SIPA solution was made and injected. A small amount of titanium catalyst was added into the partially esterified Na-SIPA solution.

Titanium catalyst solution was prepared as follows. Ethylene glycol (EG; 680 g) and KTPP (25 g) were charged to a large glass beaker and agitated 1 hour at 60° C. to produce a clear solution, to which was added 95 g of TPT to produce about 800 g of a clear solution containing 2% Ti with P/Ti molar ratio 0.5.

EG (119 kg), Na-SIPA (80 kg, from Taoka Chemical Co., Osaka, Japan), and sodium acetate (400 g) were added to a mix tank to produce a slurry as in EXAMPLE 6. Titanium catalyst described above (800 g) was added to the slurry in the mix tank. It took 60 minutes to heat the agitated slurry from 32° C. to 179° C. Na-SIPA was completely dissolved. After heating at 184° C. for 135 minutes, heating was stopped. Sample was taken 6 hours later at 126° C. When the sample was cooled, gel formed. Carboxyl groups COOH were analyzed to be 185 meq/kg (94.1% COOH esterified), 0.61% DEG, and 0.81% water. Polydimethylsiloxane (80 g) was added to the solution in the agitated mix tank. The solution was then pumped to a feed tank. The partially esterified Na-SIPA solution formed gel in the feed-tank and cold pipe. The feed tank and injection piping were heated to 130° C. to dissolve all gel. The solution was then injected into TPA oligomer to make copolymer.

Sodium acetate in ethylene glycol solution of 3.569% was injected to reduce DEG in polymer at a rate of 168 ppm Na in polymer. Triethyl phosphonoacetate was injected into oligomer line at a rate of 10 ppm P in polymer. No antimony catalyst was injected into oligomer line.

The esterifier was run at 284° C., recycle ethylene glycol from esterification and polycondensation process were mixed with virgin ethylene glycol and fed into the TPA slurry tank before esterifier. The first prepolymerizer ("flasher") was 265° C. at vacuum 140 mm Hg (18.67 kPa), the second prepolymerizer was 275° C. at vacuum 45 mm Hg (6.0 kPa), the final polymerizer ("finisher") temperature was 280° C. The average of finisher pressure was 3.86 mm Hg (0.51 kPa). Polymer temperature in the transfer line from finisher to spinning machine was 285° C.

Laboratory analysis indicated: The polymer had intrinsic viscosity 0.546, and contained Na-SIPA 2.12% by mole, antimony 13 ppm, $TiO_2$ 0.292% by weight, phosphorous 18 ppm, DEG 2.05%, carboxyl group 10 meq/kg. The melt polymer was spun to POY (245 denier 68 filaments) having the properties shown in Table 1. This POY was textured and dyed with cationic dyes.

Example 8

Examples 8, 9, and 10 illustrate a continuous polymerization process to produce copolymer at 50 kg/hour. Recycle ethylene glycol was used to make TPA slurry, which would make polymer more yellow. Li-SIPA also made a polymer more yellow than that made from Na-SIPA. But the invented process of phosphonate ester and a salt of polyphosphoric acid improved polymer b color (lower yellowness). The esterification, polycondensation, and spinning process were similar to Example 4. In Example 8, a phosphonate ester was injected into oligomer.

EG (160 kg), Li-SIPA (40 kg; from Eastman Chemical, Kingsport, Tenn., U.S.A.; active ingredient 91%), and lithium acetate dihydrate (800 g) were charged to a mix tank to produce a slurry as in EXAMPLE 6. It took 45 minutes to heat the agitated slurry from 30° C. to 179° C. Li-SIPA was completely dissolved at about 100° C.

After heating at 183° C. for 2 hours, heating was stopped. Sample was taken 3 hours later at 144° C. Carboxyl groups COOH were analyzed to be 220 meq/kg (85.4% COOH esterified), DEG 0.41%, water 1.12%, Brookfield viscosity 98 cps at 20° C. The partially esterified Li-SIPA solution sample remained yellowish and clear when cooled to room temperature. Polydimethylsiloxane (50 g) was added to the solution and the solution was pumped to a feed tank. In the feed tank, solution temperature decreased to 60–80° C. Thereafter, it was injected into TPA oligomer to make copolymer.

Lithium acetate dihydrate was injected to reduce DEG in polymer at a rate of 120 ppm Li in polymer. Di(polyoxyethylene)hydroxymethyl phosphonate (HMP, from Akzo Nobel, Louisville, Ky., U.S.A.) in ethylene glycol solution of 1.859% by weight was injected into oligomer line at a rate of 30 ppm P in polymer. No antimony catalyst was injected.

TPA esterifier temperature was 284° C., recycle ethylene glycol from esterification and polycondensation process were mixed with virgin ethylene glycol to make TPA slurry. The first prepolymerizer ("flasher") was 265° C. at vacuum 140 mm Hg (18.67 kPa), the second prepolymerizer was 275° C. at vacuum 45 mm Hg (6.0 kPa), the final polymerizer ("finisher") temperature was 280° C. The average of finisher pressure was 7.43 mm Hg (1.0 kPa). Polymer temperature in the transfer line from finisher to spinning machine was 285° C.

Laboratory analysis indicated: The polymer has intrinsic viscosity 0.593, and contained 2.09% Li-SIP by mole, 12 ppm antimony, 0.034% $TiO_2$, ppm phosphorous 27, 3.04% DEG, and 42 meq/kg carboxyl group. The melt polymer was spun to POY (245 denier 68 filaments) having the properties shown in Table 1. This POY was textured and dyed with cationic dyes.

Example 9

This example shows an alkali salt of polyphosphoric acid improves polymer b color. The process was described in Example 8, except that KTPP was injected instead of HMP.

A partially esterified Li-SIPA solution made in EXAMPLE 8 was injected into oligomer line. KTPP (0.763% in ethylene glycol solution) was injected into oligomer line at a rate of 30 ppm P in polymer. No antimony catalyst was injected. The polymerization process had a finisher pressure 6.06 mm Hg (0.81 kPa), a fisher temperature of 280° C. and polymer intrinsic viscosity 0.584. This polymer contained 2.09% Li-SIP by mole, 19 ppm antimony, 0.033% $TiO_2$, 25 ppm phosphorous, 3.05% DEG, and 39 meq/kg carboxyl group. The melt polymer was spun to POY (245 denier 68 filaments) having the properties shown in Table 1. This POY was textured and dyed with cationic dyes.

Example 10

This example shows phosphonate ester TEPA improves polymer b color. The esterification, polycondensation, and spinning process were described in Example 8, except that TEPA was injected instead of HMP.

EG (160 kg), Li-SIPA (40 kg), and lithium acetate dihydrate (800 g) were added in a mix tank to produce a slurry as in EXAMPLE 8. It took 45 minutes to heat the agitated slurry from 25° C. to 181° C. Li-SIPA was completely dissolved at about 100° C. After heating at 184° C. for 2 hours, heating was stopped. Sample was taken 6 hours later at 100° C. Carboxyl groups COOH were analyzed to be 142 meq/kg (90.6% COOH esterified), DEG 0.5%, water 1.08%. The partially esterified Li-SIPA solution sample remained yellowish clear when cooled to room temperature. Polydimethylsiloxane (50 g) was added to the solution in the agitated mix tank and the solution was pumped to a feed tank, where the solution temperature decreased to 60–80° C., before it was injected into TPA oligomer to make copolymer.

TEPA in ethylene glycol solution of 1.145% by weight was injected into oligomer at a rate of 30 ppm P in polymer. The polymerization process proceeded with a finisher pressure of 6.73 mm Hg (0.9 kPa), a finisher temperature 280° C., and ploymer intrinsic viscosity 0.592. This polymer contained Li-SIP 2.08% by mole, antimony 7 ppm, $TiO_2$ 0.033% by weight, phosphorous 28 ppm, DEG 3.31%, carboxyl group 42 meq/kg. The melt polymer was spun to POY (245 denier 68 filaments) having the properties shown in Table 1. This POY was textured and dyed with cationic dyes.

TABLE 1

Optical Properties of POY

| POY[1] | L color | a color | b color | tenacity[2] | elongation at break | boil off shrinkage | dry heat shrinkage |
|---|---|---|---|---|---|---|---|
| 4 | 81.2 | −0.05 | 3.44 | 1.76 | 139% | 50.0% | 50.1% |
| 5 | 80.8 | 0.10 | 3.59 | 1.68 | 149% | 56.0% | 60.4% |
| 6 | 81.3 | 0.31 | 2.02 | 1.69 | 138% | 56.5% | —[3] |
| 7 | 86.0 | 0.30 | 2.52 | 1.69 | 127% | 55.9% | 54.9% |
| 8 | 81.0 | 0.19 | 2.95 | 1.80 | 140% | 66.9% | 68.0% |
| 9 | 80.5 | 0.37 | 2.68 | 1.81 | 136% | 65.9% | 66.4% |
| 10 | 80.8 | 0.36 | 2.69 | 1.80 | 142% | 67.6% | 68.3% |

[1]Example numbers are shown.
[2]g/denier.
[3]not determined.

Example 11

This example shows Li-SIPA- or Na-SIPA-derived copolymers have a tendency to stick on the surface of stainless steel or carbon steel, thus plugging the process equipment after a prolonged operation.

In a commercial manufacturing process producing Li-SIPA-derived copolymer at 680 to 800 kg/hr, DMT was transesterified in an ester exchanger column too produce monomer. Antimony glycolate and lithium acetate dihydrate were added into ethylene glycol before the DMT exchanger column at the rate of 100 to 200 ppm Sb and 100 to 140 ppm Li in polymer. Li-SIPEG in ethylene glycol solution which contained 20% Li-SIPEG by weight was injected into momomer at a rate of 1.35% Li-SIPA in polymer by mole. $TiO_2$ in ethylene glycol slurry (20% $TiO_2$ by weight) and phosphoric acid in ethylene glycol (10% $H_3PO_4$ by weight) solution were added into monomer line at the rate of 0.1% to 0.435% $TiO_2$ and 100 to 140 ppm P in polymer.

The continuous polycondensation process had a upflow prepolymerizer, which had a heat exchanger in the bottom, and a final polymerizer ("finisher"). The monomer was heated in the heat exchanger by a heat transfer fluid ("Dowtherm A"; from Dow Chemical, Midland, Mich., U.S.A.) from about 200° C. to about 270° C. The heat exchanger tubes were made of stainless steel.

During a 40-day continuous operation, it was found the Dowtherm A temperature gradually increased from about 285° C. to 316° C. The process was then forced to shutdown. Two-thirds of the tubes in the heat exchanger was completely plugged by degraded and carbonized black solids. Atomic absorption analysis indicated the black solids contained carbon element about 50%, titanium 7.9%, phosphorous 0.56%, manganese 0.79%, lithium 0.18%, antimony 0.37%, silicon 0.1%, sulfur 0.09%.

What is claimed is:

1. A process comprising combining an alkali metal SIPA and a glycol to produce a mixture and heating said mixture under a condition sufficient to effect the production of a partially esterified alkali metal SIPA solution wherein said alkali metal SIPA is present in said mixture in the range of from 20% to about 40% by weight.

2. A process according to claim 1 wherein said partially esterified alkali metal SIPA solution has about 50% to about 99% of the carboxyl groups in said alkali metal SIPA esterified with said glycol.

3. A process according to claim 1 wherein said partially esterified alkali metal SIPA solution has about 80% to about 95% of the carboxyl groups in said alkali metal SIPA esterified with said glycol.

4. A process according to claim 1 wherein said process is carried out in the presence of a catalytic amount of an esterification catalyst.

5. A process according to claim 3 wherein said process is carried out in the presence of a catalytic amount of a titanium-containing catalyst.

6. A process according to claim 5 wherein said titanium-containing catalyst comprises or is produced from a titanium compound having the formula of $Ti(OR)_4$; each R is independently selected from an alkyl, cycloalkyl, alkaryl, hydrocarbyl radical containing from 2 to about 18 carbon atoms per radical.

7. A process according to claim 6 wherein said titanium compound is tetraisopropyl titanate.

8. A process according to claim 1 wherein said mixture is heated to a temperature in the range of 140° C. to 190° C.

9. A process comprising contacting a partially esterified SIPA solution in a first glycol with (1) a mixture comprising a carbonyl compound and a second glycol or (2) an oligomer having 2 to about 100 repeat units derived from said carbonyl compound and said second glycol under a condition effective to produce a polymer comprising repeat units derived from said SIPA, said first glycol, said second glycol, and said carbonyl compound wherein said first glycol and said second glycol are each independently selected from the group consisting of an alkylene glycol, a polyalkylene glycol, polyoxyalkylene glycol, and combinations of two or more thereof.

10. A process according to claim 9 wherein said first glycol and said second glycol are each independently selected from the group consisting of ethylene glycol, propylene glycol, isopropylene glycol, butylene glycol, 1-methyl propylene glycol, pentylene glycol, diethylene glycol, triethylene glycol, polyoxyethylene glycol, polyoxypropylene glycol, polyoxybutylene glycol, and combinations of two or more thereof.

11. A process according to claim 9 wherein said first glycol and said second glycol are each ethylene glycol or 1,3-propanediol.

12. A process according to claim 11 wherein said carbonyl compound is terephthalic acid, dimethyl terephthalate, or combinations thereof.

13. A process according to claim 12 wherein said partially esterified SIPA is partially esterified alkali metal 5-sulfoisophthalic acid.

14. A process according to claim 12 wherein said partially esterified SIPA is partially esterified sodium 5-sulfoisophthalic acid, partially esterified lithium 5-sulfoisophthalic acid, or combinations thereof.

15. A process comprising contacting, in the presence of a phosphorus compound and a catalyst, a SIPA or partially esterified SIPA with either (a) a polymerization mixture comprising a carbonyl compound and a second glycol or (b) an oligomer having 2 to about 100 repeat units derived from said carbonyl compound and said second glycol under a condition effective to produce a polymer comprising repeat units derived from said SIPA, said first glycol, said second glycol, and said carbonyl compound wherein said first glycol and said second glycol are each independently selected from the group consisting of an alkylene glycol, a polyalkylene glycol, polyoxyalkylene glycol, and combinations of two or more thereof;

said phosphorus compound is selected from the group consisting of a polyphosphoric acid or a salt thereof, a phosphonate ester, a pyrophosphoric acid or salt thereof, a pyrophosphorous acid or salt thereof, and combinations of two or more thereof; and said phosphorus compound is introduced to said process together with or separate from said catalyst.

16. A process according to claim 15 wherein said polyphosphoric acid has the formula of $H_{n+2}P_nO_{3n+1}$; said phosphonate ester is selected from the group consisting of $(R^1O)_2P(O)ZCO_2R^1$, di(polyoxyethylene) hydroxymethyl phosphonate, and combinations thereof; n is $\geq 2$; each $R^1$ is independently selected from the group consisting of H, $C_{1-4}$ alkyl, and combinations thereof; and Z is selected from the group consisting of $C_{1-5}$ alkylene, $C_{1-5}$ alkylidene, and combinations thereof.

17. A process according to claim 15 wherein said phosphorus compound is selected from the group consisting of phosphoric acid, sodium phosphate, potassium phosphate, phosphorous acid, potassium tripolyphosphate, sodium tripolyphosphate, potassium tetrapolyphosphate, sodium pentapolyphosphate, sodium hexapolyphosphate, potassium pyrophosphate, potassium pyrophosphite, sodium pyrophosphate, sodium pyrophosphite, ethyl phosphonate, propyl phosphonate, hydroxymethyl phosphonate, di(polyoxyethylene)hydroxymethyl phosphonate, methylphosphonoacetate, ethyl methylphosphonoacetate, methyl ethylphosphonoacetate, ethyl ethylphosphonoacetate, propyl dimethylphosphonoacetate, methyl diethylphosphonoacetate, triethyl phosphonoacetate, and combinations of two or more thereof.

18. A process according to claim 15 wherein said phosphorus compound is potassium tripolyphosphate, potassium pyrophosphate, di(polyoxyethylene)hydroxymethyl phosphonate, or triethyl phosphonoacetate.

19. A process according to claim 16 wherein said first glycol and said second glycol are each independently selected from the group consisting of ethylene glycol, propylene glycol, isopropylene glycol, butylene glycol, 1-methyl propylene glycol, pentylene glycol, diethylene glycol, triethylene glycol, polyoxyethylene glycol, polyoxypropylene glycol, polyoxybutylene glycol, and combinations of two or more thereof.

20. A process according to claim 17 wherein said first glycol and said second glycol are each ethylene glycol or 1,3-propanediol.

21. A process according to claim 18 wherein said carbonyl compound is terephthalic acid, dimethyl terephthalate, or combinations thereof.

22. A process according to claim 21 wherein said first glycol and said second glycol are each ethylene glycol or 1,3-propanediol.

23. A process according to claim 22 wherein said SIPA is selected from the group consisting of 5-sulfoisophthalic acid or mono ester thereof, sodium 5-sulfoisophthalic acid or mono ester thereof, lithium 5-sulfoisophthalic acid or mono ester thereof, bis(2-hydroxyethyl)sodium 5-sulfoisophthalate, bis(2-hydroxyethyl)lithium 5-sulfoisophthalate, sodium dimethylsulfoisophthalate, lithium dimethylsulfoisophthalate, bis(3-hydroxypropyl) sodium 5-sulfoisophthalate, bis(3-hydroxypropyl)lithium 5-sulfoisophthalate; and combinations of two or more thereof.

24. A process according to claim 23 wherein said process comprising contacting said partially esterified SIPA with either (a) said polymerization mixture or (b) said oligomers, and aid partially esterified SIPA is partially esterified alkali metal 5-sulfoisophthalic acid.

25. A process according to claim 24 wherein said partially esterified SIPA is partially esterified sodium 5-sulfoisophthalic acid, partially esterified lithium 5-sulfoisophthalic acid, or combinations thereof.

26. A process according to claim 25 wherein said phosphorus compound is introduced into said process before, during, or subsequent to said contacting.

27. A process according to claim 14 wherein said process produces a polymer comprising 85 mole % to 99.1 mole % of repeat units derived from terephthalic acid or terephthalate and 0.1 mole % to 15 mole % of repeat units derived from sodium 5-sulfoisophthalic acid or lithium 5-sulfoisophthalic acid.

28. A process according to claim 26 wherein said process produces a polymer comprising 85 mole % to 99.9 mole % of repeat units derived from terephthalic acid or terephthalate and 0.1 mole % to 15 mole % of repeat units derived from sodium 5-sulfoisophthalic acid or lithium 5-sulfoisophthalic acid.

29. A process according to claim 9 wherein said process is carried out in a vessel or process equipment comprising nickel or nickel alloy surface or fluoropolymer surface.

30. A process according to claim 15 wherein said process is carried out in a vessel or process equipment comprising nickel or nickel alloy surface or fluoropolymer surface.

31. A process according to claim 24 wherein said process is carried out in a vessel or process equipment comprising nickel or nickel alloy surface or fluoropolymer surface.

32. A process according to claim 25 wherein said process is carried out in a vessel or process equipment comprising nickel or nickel alloy surface or fluoropolymer surface.

33. A process according to claim 29 wherein said vessel or process equipment comprising said nickel or nickel alloy surface having a composition that comprises either (1) nickel metal, Ni 99 to 100% by weight or (2) Ni, 25 to 85%; Mo, 0 to 30%; Fe, 0 to 50%; Cu, 0 to 33%; Cr, 0 to 24%; Si, 0 to 10%; and 0 to 5% each of trace elements Mn, Ti, Al, Co, W, Cb, V, Ta, P, and S by weight.

34. A process according to claim 30 wherein said vessel or process equipment comprising said nickel or nickel alloy surface having a composition that comprises either (1) nickel metal, Ni 99 to 100% by weight or (2) Ni, 25 to 85%; Mo, 0 to 30%; Fe, 0 to 50%; Cu, 0 to 33%; Cr, 0 to 24%; Si, 0 to 10%; and 0 to 5% each of trace elements Mn, Ti, Al, Co, W, Cb, V, Ta, P, and S by weight.

35. A process according to claim 32 wherein said vessel or process equipment comprising said nickel or nickel alloy surface having a composition that comprises either (1) nickel metal, Ni 99 to 100% by weight or (2) Ni, 25 to 85%; Mo, 0 to 30%; Fe, 0 to 50%; Cu, 0 to 33%; Cr, 0 to 24%; Si, 0 to 10%; and 0 to 5% each of trace elements Mn, Ti, Al, Co, W, Cb, V, Ta, P, and S by weight.

36. A process according to claim 29 wherein vessel or process equipment comprising said fluoropolymer selected from the group consisting of polytetrafluoroethylene, perfluroalkoxy copolymer, perfluoro ethylene-propylene copolymer, ethylene-tetrafluoroethylene, perfluoropolyether, poly-vinylidine fluoride, fluorosilicones, and combinations of two or more thereof.

37. A process according to claim 30 wherein vessel or process equipment comprising said fluoropolymer selected from the group consisting of polytetrafluoroethylene, perfluroalkoxy copolymer, perfluoro ethylene-propylene copolymer, ethylene-tetrafluoroethylene, perfluoropolyether, poly-vinylidine fluoride, fluorosilicones, and combinations of two or more thereof.

38. A process according to claim 32 wherein vessel or process equipment comprising said fluoropolymer selected from the group consisting of polytetrafluoroethylene, perfluoroalkoxy copolymer, perfluoro ethylene-propylene copolymer, ethylene-tetrafluoroethylene, perfluoropolyether, poly-vinylidine fluoride, fluorosilicones, and combinations of two or more thereof.

* * * * *